United States Patent
Gubler

(10) Patent No.: US 6,582,738 B2
(45) Date of Patent: *Jun. 24, 2003

(54) PROCESS FOR PREPARING CHEWING GUM CONTAINING A NUTRITIONAL SUPPLEMENT

(75) Inventor: Scott A. Gubler, St. George, UT (US)

(73) Assignee: Deseret Laboratories, Inc., St. George, UT (US)

(*) Notice: Subject to any disclaimer, the term of this patent is extended or adjusted under 35 U.S.C. 154(b) by 44 days.

This patent is subject to a terminal disclaimer.

(21) Appl. No.: 09/995,260

(22) Filed: Nov. 27, 2001

(65) Prior Publication Data

US 2003/0099741 A1 May 29, 2003

Related U.S. Application Data

(63) Continuation-in-part of application No. 09/394,217, filed on Sep. 13, 1999, now Pat. No. 6,322,828.

(51) Int. Cl.$^7$ .............................. A23G 3/30; A61K 9/68
(52) U.S. Cl. ............................ 426/5; 426/3; 426/285; 426/454; 424/48; 424/440; 424/441
(58) Field of Search ...................... 426/3, 285, 454, 426/5; 424/48, 440, 441

(56) References Cited

U.S. PATENT DOCUMENTS

| | | | |
|---|---|---|---|
| 4,000,321 A | 12/1976 | Mochizuki et al. | 426/5 |
| 4,161,544 A | 7/1979 | Kaul | 426/5 |
| 4,370,350 A | 1/1983 | Fisher et al. | 426/5 |
| 4,405,647 A | 9/1983 | Fisher et al. | 426/4 |
| 4,753,805 A | 6/1988 | Cherukuri et al. | 426/5 |
| 4,803,082 A | 2/1989 | Cherukuri et al. | 424/493 |
| 4,971,079 A | 11/1990 | Talapin et al. | 131/359 |
| 4,975,270 A | 12/1990 | Kehoe | 424/48 |
| 5,711,961 A | 1/1998 | Reiner et al. | 424/441 |
| 5,922,347 A | 7/1999 | Hausler et al. | 424/441 |

FOREIGN PATENT DOCUMENTS

| | | | |
|---|---|---|---|
| DE | 28 08 160 | 8/1979 | 426/5 |

*Primary Examiner*—Arthur L. Corbin
(74) *Attorney, Agent, or Firm*—Workman Nydegger Seeley

(57) ABSTRACT

A process for preparing a chewing gum tablet includes cooling a chewing gum composition to a temperature at which the gum composition is brittle, and grinding the cooled, brittle gum composition to form a chewing gum powder. The gum composition can be cooled by mixing it with a coolant, such as solid carbon dioxide, prior to grinding. The chewing gum powder is mixed with an active composition comprising a nutritional supplement, such as one or more vitamins, minerals, or herbs, to form a nutritional supplement-containing powder. The mixture of gum powder and the nutritional supplement, along with other optional additives, is then granulated to form nutritional supplement-containing granules. These granules are then compressed to form chewing gum tablets.

34 Claims, No Drawings

PROCESS FOR PREPARING CHEWING GUM CONTAINING A NUTRITIONAL SUPPLEMENT

This is a continuation-in-part of U.S. application Ser. No. 09/394,217, filed on Sep. 13, 1999, now U.S. Pat. No. 6,322,828 B1, which is incorporated herein by reference.

BACKGROUND OF THE INVENTION

1. Field of the Invention

The present invention relates to processes for producing chewing gums containing active ingredients. In particular, the present invention relates to a process for preparing a chewing gum tablet containing one or more nutritional supplements.

2. Background Technology

Conventional chewing gum processing technology involves melting a gum base in, for example, a sigma blender, and adding components such as sweeteners and flavorants to the melt. The melted mass is then extruded, rolled into sheets, and cut to the desired shape on the rollers. This conventional technology, however, suffers from several disadvantages when applied to the preparation of chewing gums containing active ingredients. For example, the elevated temperatures used in forming the melt can adversely affect the chemical stability of any active ingredients contained therein. In addition, the melting and mixing process for the highly viscous gum mass makes controlling the accuracy and uniformity of the amount of active ingredient difficult, and this difficulty is further exacerbated by the lack of a precise form, shape or weight of the gum product. In addition, conventional gum processing technology is generally poorly suited for high-speed, low cost production of gum products having active ingredients.

Several patents are directed to methods of processing chewing gums which attempt to overcome some of the disadvantages described above. For example, U.S. Pat. No. 4,000,321 to Mochizuki et al. is directed to a process for preparing chewing gum, in which a chewing gum composition is cooled to −15° C. to facilitate fragmentation, and the cooled composition is pulverized with a crusher, hammer mill, pelletizer or turbomill. The pulverized product is then melted to cause the pulverized pieces to co-adhere, forming a chewing gum reportedly having low specific gravity and a soft chewing texture. The process, however, suffers from all of the disadvantages associated with heating, process speed, poorly defined forms and weights described above, and is not well-suited for making a chewing gum dosage form containing an active ingredient.

U.S. Pat. No. 5,711,961 to Reiner et al. discloses a pharmaceutical chewing gum composition in tablet form made by freezing chewing gum, grinding the gum in a mill, and granulating the ground gum in a fluid bed. Thereafter, a medicinal active agent is mixed with the granulate, and the granulates are compressed into tablets.

In U.S. Pat. No. 4,975,270 to Kehoe, a medicament-active chewing gum is disclosed which is made by freezing and grinding into a particle mass an elastomer, an active agent, and silica in the presence of liquefied carbon dioxide. The particles are then shaped into a chewing gum product. In the process of Kehoe, the gum and the active ingredient are mixed together while heating, and then the mixture is frozen and ground into particles.

In U.S. Pat. No. 4,753,805 to Cherukuri et al. a chewing gum composition in the form of a tablet having a low moisture content is disclosed. The tablet is produced by grinding a chewing gum composition, granulating the ground composition, blending the granulated composition with an active agent and a compression aid, and compressing the granulated product to form a tablet. Grinding of the chewing gum composition, typically a difficult process because of the tendency for the gum to stick to the grinding apparatus, is accomplished by the use of a grinding aid such as an alkaline metal phosphate, an alkaline earth metal phosphate, or a maltodextrin. The use of such grinding aids, however, is disadvantageous. The metal phosphate salts are highly alkaline, and such alkalinity may be incompatible with certain active ingredients. In addition, the grinding aid remains in the composition and ultimately in the chewing gum tablet, and the presence of a large amount of metal phosphate is potentially problematic from therapeutic and safety perspectives.

Thus, there is a need for processes to produce active-containing chewing gums that do not suffer from the disadvantages of conventional active-containing chewing gum formulations.

SUMMARY OF THE INVENTION

The present invention relates to a process for preparing a chewing gum tablet containing a nutritional supplement and the resulting chewing gum tablet product. The process of the invention includes cooling a chewing gum composition to a temperature at which the gum composition is brittle, and grinding the cooled, brittle gum composition to form a chewing gum powder. The composition can be cooled by mixing it with a coolant, such as solid carbon dioxide, prior to grinding. The chewing gum powder is mixed with an active composition comprising a nutritional supplement, such as one or more vitamins, minerals, or herbs, to form a nutritional supplement-containing powder. The mixture of powder and nutritional supplement, along with other optional additives, is then granulated to form nutritional supplement-containing granules. These granules are then compressed to form chewing gum tablets.

In another aspect, the present invention is directed to a chewing gum tablet comprising a plurality of granulated particles compressed to form the tablet. The granulated particles comprise a chewing gum composition and a nutritional supplement, along with any other ingredients added during processing to form the tablet. The granules forming the tablet can be of a size suitable for tabletization methods.

These and other features of the present invention will become more fully apparent from the following description and appended claims, or may be learned by the practice of the invention as set forth hereinafter.

DETAILED DESCRIPTION OF THE INVENTION

The present invention is directed to a process for preparing a chewing gum tablet containing a nutritional supplement and the resulting chewing gum tablet product. The process of the invention generally includes cooling a chewing gum composition to a temperature at which the composition is brittle, and grinding the cooled, brittle chewing gum composition to form a chewing gum powder. The chewing gum powder is mixed with a nutritional supplement, such as one or more vitamins, minerals, or herbs, to form a nutritional supplement-containing powder. The mixture of chewing gum powder and nutritional supplement, along with other optional additives, is then granulated to form nutritional supplement-containing granules. These granules are then compressed to form chewing gum tablets. Each of these process steps will be discussed in further detail as follows.

In an initial step of the process of the invention, a chewing gum composition is cooled to a temperature at which the composition is brittle. The chewing gum composition can be any chewing gum formulation, such as conventional gum compositions known in the art. In general, such gum compositions include a chewing gum base, to which may be added conventional flavorants, sweeteners, colorants, and other ingredients known in the art. The chewing gum base is typically a natural or synthetic elastomer, such as rubber, chicle, lechi caspi, jelutong, polyisobutylene, an isobutylene-isoprene copolymer, a styrene-butadiene copolymer, or other suitable gum bases known in the art. In order to facilitate the subsequent grinding step, the chewing gum composition is preferably in the form of chips, pellets, or other relatively small particles.

In cooling the chewing gum composition to a temperature at which the composition is brittle, it should be appreciated that even a mildly cooled chewing gum composition will possess some degree of brittleness. However, to be suitable for the process of the present invention, the composition is cooled to a temperature at which the composition is sufficiently brittle such that the brittleness is maintained during the subsequent grinding step without adhesion to the grinding apparatus. The appropriate temperature is determined in part by the specific composition of the chewing gum, and is easily determined empirically by observing the properties of the cooled chewing gum composition. Thus, a chewing gum composition cooled to a temperature sufficiently low can be ground in, for example, a mill grinder, without the composition sticking to the grinder parts. The chewing gum composition can be cooled to a temperature of less than about −15° C., preferably less than about −30° C., and more preferably less than about −40° C.

The cooling of the gum composition can be carried out by any of a variety of cooling processes. The chewing gum composition can be frozen in a conventional freezer apparatus capable of reaching the very low temperatures needed to achieve the requisite brittleness. Preferably, however, the chewing gum composition is cooled by contacting it with a coolant. The coolant can be any substance capable of cooling the chewing gum composition to the desired temperature and can be, for example, a cryogenic liquid such as liquid nitrogen, a cold solid such as solid carbon dioxide, or a cold gas such as the gaseous boil-off from a cryogenic liquid. The coolant should be chosen so that the coolant does not interact adversely with the chewing gum composition or with the mixing or grinding apparatus used in the present process. In addition, the coolant should not produce a substance that upon warming produces such adverse interactions, or that leaves a residue that adversely affects subsequent processing or presents potential safety hazards when the chewing gum tablet is chewed. For example, a coolant such as water ice, even if cooled to a sufficiently low temperature, would not be preferred, as any water ice that melts will form liquid water, which is absorbed by the chewing gum composition. Likewise, a coolant such as a hydrocarbon slush would not be preferred, since any hydrocarbon residue remaining in the chewing gum composition would present potential safety hazards when the chewing gum tablet is consumed.

In accordance with the present invention, and in a particularly preferred aspect, it has been surprisingly found that by mixing a chewing gum composition with solid carbon dioxide (dry ice), the chewing gum composition can be cooled to a brittle temperature without the undesirable effects discussed above. At the sublimation temperature, −78.5° C., solid carbon dioxide is sufficiently cold to ensure that the chewing gum composition is suitably brittle. Of course, the solid carbon dioxide can be cooled to an even lower temperature, if desired. Upon warming, the solid carbon dioxide sublimes to form carbon dioxide gas, which does not react with the chewing gum composition, is not absorbed by the composition, and does not interact adversely with processing apparatuses. Further, the gaseous, non-reactive nature of the sublimation product ensures that no undesirable and potentially hazardous residue of the coolant remains in the chewing gum tablet product. Preferably, the solid carbon dioxide coolant is provided in pelletized form to facilitate further processing steps.

Alternatively, the steps of cooling the chewing gum composition and grinding the composition can be combined into a single step by, for example, cooling the grinding apparatus itself, such as by contacting the grinding apparatus with a coolant. For example, in this alternative aspect, the grinding apparatus can be placed in a cooling jacket of liquid nitrogen or other cold liquid. For more efficient cooling, in this embodiment, the chewing gum composition is preferably pre-cooled, although the pre-cooling need not be to a temperature as low as the brittle temperature. It should be appreciated that even in the embodiment where the chewing gum composition is cooled my mixing it with a coolant, it may also be advantageous to cool the grinding apparatus as well.

If desired, the chewing gum composition can be mixed with an anti-caking agent prior to the grinding step. Such anti-caking agents are known in the art. A preferred anti-caking agent is precipitated silicon dioxide (silica). When the chewing gum composition is mixed with solid carbon dioxide and an anti-caking agent prior to grinding, the anti-caking agent helps to prevent agglomeration of the subsequently ground chewing gum particles, upon sublimation of the solid carbon dioxide.

If a coolant, such as solid carbon dioxide, and other components, such as an anti-caking agent are used, the chewing gum composition and other substances can be combined using a conventional mixing apparatus, such as a vented V-blender.

The mixture of the chewing gum composition, and other components such as coolant and anti-caking agent, is then ground to form a fine chewing gum powder. The grinding can be carried out using any conventional grinding apparatus, such as a mill grinder. In one embodiment, a mixture of a chewing gum composition, solid carbon dioxide, and precipitated silica is provided, and the mixture is introduced into a mill grinder. The mixture is ground to a fine powder, and the solid carbon dioxide remains present during the grinding process. It has been surprisingly found that by co-grinding the chewing gum composition and solid carbon dioxide, the chewing gum composition can be ground into a fine powder, without any adverse adhesion to the grinding apparatus.

The desired properties of the ground chewing gum composition are better achieved when the composition is kept at a very low temperature throughout the grinding process. Thus, in a particularly preferred process, a mixture of chewing gum composition, solid carbon dioxide and precipitated silica is ground in a mill grinder in a first grinding step, additional solid carbon dioxide and precipitated silica are added to the ground mixture, and the mixture is further ground in a second grinding step. This two-step grinding process advantageously keeps the chewing gum composition at a very low temperature. Although not wishing to be bound by theory, it is further believed that the presence of the solid carbon dioxide particles, in addition to providing the necessary cooling, also serves to enhance the efficiency of the grinding process. It should be appreciated that although a two-step grinding process is described herein, the number of steps is not particularly limited. Thus, a process in which additional solid carbon dioxide and/or precipitated silica are added in multiple steps, or even in a slow, continuous stream, may also be used if desired.

After the mixture is ground to a powder, the coolant can be removed by, for example, allowing the coolant to evaporate. When using solid carbon dioxide, the coolant is removed simply by allowing the solid carbon dioxide to sublime, releasing harmless carbon dioxide gas and leaving no undesirable contaminants. The ground composition can be stored such that the carbon dioxide gas can escape, as for example in loosely closed plastic bags. Alternatively, the carbon dioxide can be removed more rapidly by processing the ground composition in a fluidized bed reactor.

Once the coolant has been removed from the chewing gum powder, the powder is mixed with an active composition comprising a nutritional supplement to form a nutritional supplement-containing powder. The nutritional supplement can include one or more active ingredients such as vitamins, mineral nutrients, herbs, other natural products having nutritional value, such as essential amino acids, as well as various mixtures or combinations thereof.

Examples of suitable vitamins for the nutritional supplement include vitamin A, vitamin C, vitamin D, vitamin E, vitamin K, vitamin $B_6$, vitamin $B_{12}$, thiamine, riboflavin, biotin, folic acid, niacin, pantothenic acid, and mixtures thereof. Examples of suitable mineral nutrients include those having one or more elements selected from sodium, potassium, calcium, magnesium, phosphorus, sulfur, chorine, iron, copper, iodine, zinc, selenium, manganese, chromium, molybdenum, fluorine, cobalt, and combinations thereof.

Various herbs can be utilized in the nutritional supplement. The herbs are generally selected from those which have various medicinal or dietary supplement properties. Herbs are generally aromatic plants or plant parts that can be used medicinally or for flavoring. Suitable herbs can be used singly or in various mixtures in the chewing gum composition of the invention.

The chewing gum powder can also be mixed with other ingredients as desired, before forming the powder into a tablet. Such ingredients can be any ingredient known to be incorporated into chewing gum and not incompatible with tablet formation, such as coating agents, binders, lubricants, sweeteners, as well as other active ingredients, and the like.

The foregoing ingredients can be combined with the chewing gum powder by blending, such as in a sigma mill, or a high shear mixer. If a conventional blending apparatus is used, the powder mixture can include sufficient amounts of binder to enable effective processing of the mixture. Such binders, well-known in the art, are typically aqueous, and the large amounts of aqueous binder necessary to enable tabletization from a blended mixture are not preferred, as the mixture tends to swell and to develop a disadvantageous stickiness that makes tabletization less efficient. However, although not preferred, such blending processes can still be used in the process of the present invention.

In a preferred process, it has been surprisingly found that the powdered chewing gum produced by the process described above can be combined with other ingredients, such as nutritional supplements and other additives, in a fluidized bed reactor. The use of a fluidized bed reactor is particularly advantageous, as the process in the reactor partially rebuilds the powder into granules, as well as coats the powder particles and/or granules with a coating agent if used, thereby minimizing undesired particle agglomeration. In this embodiment, the temperature of the process should be controlled. If the temperature is too low, the mixture (the "blend") will stick because of a low evaporation rate as the binding solution is sprayed on the blend. The granules that develop are then too large for subsequent tabletization. If the temperature is too high, the blend can soften, with the same disadvantageous results. With these considerations in mind, one skilled in the art can readily determine the appropriate process temperature by observing and optimizing the properties of the granules produced. To reduce the processing time, the fluid bed granulator can be pre-heated to the chosen processing temperature prior to adding the powder mixture. After granulation, the granulate can be discharged onto screens, and any granules that are too large can be removed.

In a preferred process, the powder mixture, containing the powdered chewing gum composition, nutritional supplement, and other additives, is weighed into individual "charges" for the fluid bed granulator. After processing as described above, and screening, the individual charges are then preferably recombined and mixed in a V-blender, and the resultant "cross-blend" is then discharged across a screen to again remove any granules that are too large. It is particularly advantageous to sample the cross-blend discharge by taking multiple samples from the discharge stream, for analysis of the nutritional supplement. Thus, the discharge mixture can be stored while the multiple samples are analyzed, to ensure that the desired level and uniformity of level of the nutritional supplement are present. If necessary, additional amounts of the nutritional supplement can then be added to the mixture.

The discharge mixture is again placed in a V-blender, and any additional nutritional supplement is added. In addition, an anti-adherent is preferably added at this time, along with any other desired excipients or inactive ingredients. A preferred anti-adherent is talc. The mixture can then be discharged, again screened, and staged for compression.

The compression of the granules to form tablets can be carried out by any conventional process, such as a punching process. Of course, the punching process should be monitored for signs of sticking to the punches, and the apparatus cleaned, and/or coated with additional anti-adherent as needed.

By granulating the gum powder after mixing it with the nutritional supplement, the gum powder and the nutritional supplement are bound together in the granules, which prevents separation of the nutritional supplement from the gum powder during the tablet forming process. Thus, a more even mix of gum particles and nutritional supplement are present in the formed gum tablets.

The process of the present invention results in chewing gum tablets that are precisely and uniformly formed in a well-defined shape and weight. The process for preparing the chewing gum tablets is also capable of being carried out in high-speed and efficient manufacturing facilities.

In another aspect, the present invention is directed to a chewing gum tablet comprising a plurality of granulated particles compressed to form the tablet. The granulated particles comprise a chewing gum composition and a nutritional supplement, along with any other ingredients added during processing to form the tablet. The granules forming the tablet can be of a size suitable for tabletization, typically from about 15 mesh to about 30 mesh, and preferably from about 20 mesh to about 25 mesh. The chewing gum tablets of the invention can be produced by any of the methods described above. Advantageously, the tablets do not contain any residue of a grinding aid, such as an alkaline phosphate used in conventional methods.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A process for preparing a chewing gum tablet, the process comprising:

cooling a chewing gum composition to a temperature at which the gum composition is brittle;

grinding the cooled chewing gum composition to form a chewing gum powder;

mixing the chewing gum powder with an active composition comprising a nutritional supplement to form a nutritional supplement-containing powder;

granulating the nutritional supplement-containing powder to form a plurality of nutritional supplement-containing granules; and forming the nutritional supplement-containing granules into one or more chewing gum tablets.

2. The process of claim 1, wherein the cooling of the chewing gum composition comprises contacting the chewing gum composition with a coolant comprising a non-reactive substance capable of cooling the chewing gum composition to the brittle temperature.

3. The process of claim 2, wherein the coolant comprises solid carbon dioxide.

4. The process of claim 1, wherein the grinding of the cooled chewing gum composition is carried out in the presence of a coolant in contact with the chewing gum composition, the coolant comprising a non-reactive substance.

5. The process of claim 4, wherein the coolant comprises solid carbon dioxide.

6. The process of claim 1, wherein the cooling and grinding are carried out by mixing the chewing gum composition with solid carbon dioxide and grinding the chewing gum and solid carbon dioxide mixture.

7. The process of claim 6, wherein the chewing gum composition is mixed with solid carbon dioxide and an anti-caking agent.

8. The process of claim 1, wherein the cooling and grinding are carried out by:

providing a mixture of the chewing gum composition, solid carbon dioxide, and an anti-caking agent;

grinding the mixture in a first grinding step;

adding additional amounts of solid carbon dioxide and anti-caking agent to the ground mixture; and further grinding the mixture in a second grinding step.

9. The process of claim 8, wherein the anti-caking agent comprises precipitated silicon dioxide.

10. The process of claim 1, wherein the chewing gum composition is cooled to a temperature below about −30° C.

11. The process of claim 1, wherein the granulating is carried out in a fluid bed granulator.

12. The process of claim 11, further comprising coating the nutritional supplement-containing powder in the fluid bed granulator with a coating agent.

13. The process of claim 1, wherein the chewing gum powder is mixed with one or more additives prior to granulating, the additives selected from the group consisting of coating agents, binders, lubricants, and sweeteners.

14. The process of claim 1, wherein the nutritional supplement comprises one or more vitamins.

15. The process of claim 14, wherein the one or more vitamins are selected from the group consisting of vitamin A, vitamin C, vitamin D, vitamin E, vitamin K, vitamin $B_6$, vitamin $B_{12}$, thiamine, riboflavin, biotin, folic acid, niacin, pantothenic acid, and mixtures thereof.

16. The process of claim 1, wherein the nutritional supplement comprises one or more mineral nutrients.

17. The process of claim 16, wherein the one or more mineral nutrients comprise one or more elements selected from the group consisting of sodium, potassium, calcium, magnesium, phosphorus, sulfur, chorine, iron, copper, iodine, zinc, selenium, manganese, chromium, molybdenum, fluorine, cobalt, and combinations thereof.

18. The process of claim 1, wherein the nutritional supplement comprises one or more vitamins and one or more mineral nutrients.

19. The process of claim 1, wherein the nutritional supplement comprises one or more herbs.

20. The process of claim 19, wherein the nutritional supplement comprises a mixture of different herbs.

21. The process of claim 1, wherein the nutritional supplement-containing granules have an average size of about 15 mesh to about 30 mesh.

22. A process for preparing a chewing gum tablet, the process comprising:

providing a mixture comprising a chewing gum composition and solid carbon dioxide;

grinding the mixture to form a chewing gum powder;

removing the solid carbon dioxide from the chewing gum powder;

mixing the chewing gum powder with an active composition comprising a nutritional supplement to form a nutritional supplement-containing powder;

granulating the nutritional supplement-containing powder to form a plurality of nutritional supplement-containing granules; and compressing the nutritional supplement-containing granules into one or more chewing gum tablets.

23. The process of claim 22, wherein the mixture further comprises an anti-caking agent.

24. The process of claim 23, wherein the anti-caking agent comprises precipitated silicon dioxide.

25. The process of claim 23, wherein the grinding step comprises:

grinding the mixture in a first grinding step;

adding additional amounts of solid carbon dioxide and anti-caking agent to the ground mixture; and further grinding the ground mixture in a second grinding step to form the chewing gum powder.

26. The process of claim 22, wherein the removing of the solid carbon dioxide from the chewing gum powder comprises storing the chewing gum powder for a sufficient time such that substantially all of the solid carbon dioxide sublimes.

27. The process of claim 22, wherein the removing of the solid carbon dioxide from the chewing gum powder comprises processing the chewing gum powder and the solid carbon dioxide in a fluid bed granulator.

28. The process of claim 22, wherein the chewing gum powder is mixed with one or more additives prior to granulating, the additives selected from the group consisting of coating agents, binders, lubricants, and sweeteners.

29. The process of claim 22, wherein the nutritional supplement comprises one or more vitamins.

30. The process of claim 29, wherein the one or more vitamins are selected from the group consisting of vitamin A, vitamin C, vitamin D, vitamin E, vitamin K, vitamin $B_6$, vitamin $B_{12}$, thiamine, riboflavin, biotin, folic acid, niacin, pantothenic acid, and mixtures thereof.

31. The process of claim 22, wherein the nutritional supplement comprises one or more mineral nutrients.

32. The process of claim 31, wherein the one or more mineral nutrients comprise one or more elements selected from the group consisting of sodium, potassium, calcium, magnesium, phosphorus, sulfur, chorine, iron, copper, iodine, zinc, selenium, manganese, chromium, molybdenum, fluorine, cobalt, and combinations thereof.

33. The process of claim 22, wherein the nutritional supplement comprises one or more vitamins and one or more mineral nutrients.

34. The process of claim 22, wherein the nutritional supplement comprises one or more herbs.

* * * * *